United States Patent [19]
Kishida

[11] Patent Number: 5,846,928
[45] Date of Patent: Dec. 8, 1998

[54] METHOD FOR TREATING CANCER PATIENTS

[75] Inventor: Tsunataro Kishida, Kyoto, Japan

[73] Assignee: PasKen Products Co., Ltd., Kyoto, Japan

[21] Appl. No.: 691,122

[22] Filed: Aug. 1, 1996

[51] Int. Cl.⁶ .................................................. A01N 37/18
[52] U.S. Cl. ................................................................ 514/2
[58] Field of Search ..................................... 514/2

[56] References Cited

PUBLICATIONS

Alimean, G. et al., Eur. J. Haemol., 43(2) pp. 108–111, 1989, see abstract.
Giardina, S. L. et al., Blood, 72(5), pp. 1798–1716, 1988, see abstract.
Eischen, A. et al., J. Immunol. Methods 143(2), pp. 209–221, 1991, see abstract.
Collins, R. H. et al., Transfusion(Bethesda) 35(11), pp.891–898, 1995, see abstract.

*Primary Examiner*—Marianne M. Cintins
*Assistant Examiner*—Dwayne C. Jones
*Attorney, Agent, or Firm*—Burgess, Ryan & Wayne

[57] ABSTRACT

A new immunotherapy to cancer patients is provided. In the therapy, lymphocytes collected from a patient by leukopheresis are treated with interferon-α in vitro for a short period of term and then returned to the patient intravenously. According to the therapy, reduction in sensitivity of tumor cells to natural killer-cell lysis due to administration of interferon-α is eliminated, the activities of NK cell and 2-5AS and interferon-producing capacity can be enhanced, a large amount of lymphocytes can be activated directly in vitro with the dose of optimally adjusted to the patient, none of side effects are found, and any other potentiators and comodulaators, which may not be allowed to use in vivo, can be added to the lymphocytes and removed therefrom before returning to the patient.

21 Claims, No Drawings

METHOD FOR TREATING CANCER PATIENTS

TECHNICAL FIELD

The invention pertains to immunotherapy to cancer patients employing lymphocytes activated with interferon-α.

BACKGROUND OF THE INVENTION

Interferon (IFN) is known to have antitumor activity through two major mechanisms, a direct cytotoxic effect by IFN on the tumor cells and an indirect cytotoxic effect through the activation of natural killer (NK) cells, macrophages or other immune cells of the host system. Activation of NK cells and other immune cells with IFN administration has been reported to be effective in the treatment of a wide variety of tumors. However, this very treatment decreases sensitivity of tumor cells to NK cell lysis due to an increase in expression of HLA antigen and sugar chains on the surface of tumor cells (Trincheri G., et. al., J. Exp. Med., 1314–1333, 1978). Moreover, high-dose IFN-α administration to patients with myclocytic leukemia or renal cancer has been reported to cause severe side effects such as fever, malaise, depilation and depression in some cases, which significantly affect the patients (Quesada JR, et. al., J. Clin Onco 4: 234–243, 1986).

In recent years, lymphokine-activated killer cell (LAK) therapy has been conducted in large scale clinical studies wherein lymphocytes taken outside of the body were activated using interleukin-2 (IL-2) and subsequently injected back into the body. Results from these studies have been reported to be promising but there yet remain many problems to overcome, especially in terms of cost/effectiveness and occurrence of side effects (Rosenberg, S. A., et. al.; N. Engl. J. Med. 313: 1485, 1985).

BRIEF DESCRIPTION OF THE INVENTION

The present inventors were interested in the potential of a new approach of immunotherapy using IFN-activated lymphocytes in improving the effectiveness of treatment to patients with cancer. In order to eliminate sensitivity reduction of tumor cells to NK cell lysis due to in vivo IFN administration, the inventors have aimed at the efficient activation of immune cells, mainly HK cells through in vitro IFN treatment, and designated this treatment as interferon-activated-NK-lymphocyte (IFNANK) therapy.

Briefly, lymphocytes are collected from a patient by leukopheresis, treated with IFN-α in vitro for a short term, and thereafter returned to the patient.

NK cell activity, 2-5AS ((2'-5')oligoadenylate synthetase) activity and IFN-α producing capacity before and after the therapy were monitored to evaluate the effectiveness of the therapy. Among the cancer patients who received the therapy, the augmentation of this ability and capacity were proved in about half of the patients and none of the patients experienced any side effects.

The present invention is directed to a method for treating a patient with cancer, which comprises collecting lymphocytes from the patient by leukopheresis, contacting the lymphocytes with interferon-α in vitro for a short term which is effective to potentiate the immunological activity of the lymphocytes, and then returning the lymphocytes to the patient intravenously.

DETAILED DESCRIPTION OF THE INVENTION

The present method is applicable to a patient suffering from any kind of cancer such as gastric cancer, ovarian cancer, cervical cancer, adenocarcinoma, small cell carcinoma, melanoma, leukemia, etc.

Leukopheresis can be carried out using a commercially available intermittent or continuous flow cell separators for separating blood components. In the rotary chamber of the separator, peripheral blood of a patient with an anti-coagulant such as citrate is centrifuged for a short term, thereby lymphocyte-rich fraction containing leukocytes is collected into a collection bag.

After or during the collection, IFN-α is added to the bag in an amount to make a final concentration of not less than 100 IU/ml, preferably about 300–500 IU/ml to contact with lymphocytes. By gentle stirring the mixture for 0.5 to 1.5 hours, preferably about 30 min. at room temperature, the lymphocytes are effectively potentiated and can be returned to the patient intravenously.

The results obtained by the present method in Example 2 and Table 2 are summarized in the following;

None of the subjects treated by present method experienced any side effects. On the other hand, high-dose administration which is commonly used in patients with hepatitis C or cancer has been reported to cause severe side effects such as fever in more than 50% of cases, and malaise, depilation, leukopenia or thrombocytopenia in 10–30% of cases. No side effects, however, appeared in the present method.

In terms of immunological potentiation, NK cell activity was enhanced in 3 out of 4 healthy controls, and about half of the cases of cancer patients. Especially focused on the initial trial, 6 out of 8 cancer patients revealed augmented NK cell activity, although in some of those cases, increased rate of HK activity was lowered in the subsequent treatments. This fluctuation in the activity seems to be attributed to the individual difference in sensitivity to IFN-α, which may be related to the progress of cancer.

Increased 2-5AS activity was observed in most of the trials, although not always paralleled with the results of increased NK cell activity. 2-5AS activity may be considered as a more useful parameter to evaluate the sensitivity to IFN-α in an individual patient than OK cell activity (Shindo, M. et. al.;

Hepatology 8, 366–370, 1988).

Enhancement of IFN-α producing capacity, in the initial trial, was observed in 6 out of 8 cancer patients and in 3 out of 4 healthy controls. IFN-producing capacity has been reported to decrease with the progression of disease in patients with lung or bladder cancer (Kou J, Y, et. al.; Urol Res. 19:51–56, 1991; Onodera, H. et. al.; J. IFN Res., Suppl. 1: S132, 1993). An increase of IFN-α producing capacity may be a promising sign for the patients.

According to present invention, (1) a large amount of lymphocytes (up to $5 \times 10^9$) can be activated directly in the collection bag with the dose of IFN-α optimally adjusted to the patient, (2) no side effects are found, and (3) any other potentiators and comodulators, which may not be allowed for use in vivo, can be added in the bag. By removing them from the activated lymphocytes before re-injection, it is possible to make the lymphocytes harmless to the patient.

EXAMPLE 1

(Preliminary in vitro experiment to determine the optimal dose of IFN-α to augment the NK cell ability)

To find out an optimal concentration of IFN, a leukocyte fraction containing lyphocytes separated by leukopheresis were resuspended in RPMI 1640 medium supplemented with 10% fetal calf serum and adjusted to a concentration of $5 \times 10^6$ cells/ml, and cultured with 0–1000 IU/ml human leukocyte IFN-α cells for 18 hours in a humidified incubator at 37° C. with 5% $CO_2$. Peripheral blood mononuclear cells (PBMCs) were isolated by Ficoll-Hypaque density gradient centrifugation. For the measurement of NK cell activity, K562 cells derived from erythroleukemia cell line, were used as target cells and were labeled with europium, whereas PBMCs were used as effector cells. NK cell activity was measured by the ability of PBMCs to induce release of the europium from lysed K562 cells and the results are expressed in the following Table as percentage cytotoxicity.

| NK cell activity treated with various doses of IFN-α in vitro | |
|---|---|
| IFN (IU/ml) | NK activity (%) |
| 0 | 16.4 |
| 10 | 26 |
| 100 | 45.1 |
| 1000 | 45.6 |

As seen from the above Table, lymphocytes are activated in a dose dependent manner by treating in vitro with IFN-α in the range of concentration from 1 to 1000 units/ml of IFN-α. Lymphocytes activation with 1000 IU/ml of IFN-α revealed a similar result to that of 100 IU/ml of IFN-α, indicating the activation reaches the plateau at 100 IU/ml of IFN-α. Therefore, for contacting lymphocytes with IFN-α, it is preferred to add IFN-α in an amount sufficient to make a final concentration of not less than 100 IU/ml, more preferably 300 to 500 IU/ml to the lymphocytes.

EXAMPLE 2
(Lymphocyte collection and its activation with IFN)
Subjects: Four healthy controls and 8 cancer patients who all received IFNANK therapy for a total twenty-six times. Patients' profiles are shown in Table 1.

To obtain a large number of lymphocytes, leukopheresis was carried out using SPECTRA® (a blood cell collection device produced by COBE Inc., U.S.A.) in the following manner. 2000–4000 ml of peripheral blood was centrifuged in the system at a flow rate of 40–60 ml/min. for about 1–1.5 hour, and 200–300 ml of lymphocyte-rich fraction containing ACD acid citrate dextrose) as a anti-coagulant was collected in the bag. Approximately $2–7 \times 10^9$ leukocytes containing 50–80% lymphocytes were recovered in the bag. After or during the collection, $1 \times 10^5$ IU of IFN-α was added into the bag, which corresponds to a final concentration of 400–500 IU/ml. After gentle stirring for 30 min. at room temperature, "activated lymphocytes" were returned to the subject intravenously.

Samples of peripheral blood were extracted from the subjects intravenously before IFNANK therapy and up to 96 hours after the therapy, in order to monitor NK cell activity, IFN-α producing capacity and 2'5'A oligoadenylate (2-5A) synthetase activity in the whole blood.

IFN-producing capacity was measured using whole blood method (Kou J. Y. et. al. Urol Res. 19: 51–56, 1991).

For the measurement of 2-5A synthetase activity, samples of heparinized peripheral blood were stored at 80° C. until measurement. After thawing, 2-5A synthetase activity was measured using "25A" kit (Eiken Co. Ltd., Japan).

For measuring IFN-α producing capacity, samples of heparinized peripheral blood were incubated with Sendai virus at 37° C. for 20 hours, thereafter IFN-α activity was measured by bioassay (Kohase M, et. al. Japan Medical Foundation Publication No. 15: 299–309, 1982)

TABLE 1

(Patients' profile)

| | Sex | Age | Diagnosis | Medical background |
|---|---|---|---|---|
| H T | male | 68 | gastric cancer | gastrectomy, 1992 (stage IV) recurrence and reoperation, 1994 (stage IV) |
| Y T | male | 44 | adenocarcinoma, lung | operation, 1993 (stage III) recurrence, 1994 (stage IV) |
| M T | female | 53 | cervical cancer | operation, 1994 (stage II) |
| N K | male | 39 | adenocarcinoma, lung | operation, 1994 (stage III) recurrence, 1995 (stage IV); radiation, chemotherapy |
| T A | female | 47 | ATL | mycosis fungoides was diagnosed in 1992 |
| Y M | female | 65 | melanoma | first diagnosis, 1992 (stage IV); chemotherapy |
| Y M | female | 58 | small cell carcinoma, lung | radiation and chemotherapy (stage III), complete remission |
| H M | female | 41 | ovarian cancer | operation, 1994 (stage III); recurrence (stage IV) |

TABLE 2-a

Results of IFNANK therapy

| IFNANK times | Days from first trial | No. of WBC($\times 10^9$) treated with IFN (Lymphocytes $\times 10^9$) | TBVL* | Days after IFNANK | IFN-α production | 2-5AS activity (pmol/dl) | NK activity (%) | WBC (/μl) | Hb (g/dl) | Plt ($\times 10/\mu l$) | Side effect** |
|---|---|---|---|---|---|---|---|---|---|---|---|
| | | | | HT, Gastric cancer, male, 68 | | | | | | | |
| 1st | 0 | 3.9 (2.4) | 2000 ml | 0 d | 4086 | 4440 | 5 | 6400 | 10.5 | | ND |
| | | | | 1 d | 3798 | 7860 | 26 | | | | |
| | | | | 4 d | 7097 | 5790 | 38 | | | | |

TABLE 2-a-continued

Results of IFNANK therapy

| IFNANK times | Days from first trial | No. of WBC(× 10⁹) treated with IFN (Lymphocytes × 10⁹) | TBVL* | Days after IFNANK | IFN-α production | 2-5AS activity (pmol/dl) | NK activity (%) | WBC (/μl) | Hb (g/dl) | Pit (× 10/μl) | Side effect** |
|---|---|---|---|---|---|---|---|---|---|---|---|
| 2nd | 76 | 2.9 (2.1) | 2448 ml | 0 d | 1519 | 4020 | 31 | 7200 | 13.5 | 34.7 | ND |
|  |  |  |  | 2 d | 4447 | 3450 | 59 | 6400 | 11.4 | 35.4 |  |
| 3rd | 130 | 3.9 (2.8) | 3000 ml | 0 d | 1946 | 4950 | 31 | 6300 | 10.8 | 37.2 | ND |
|  |  |  |  | 1 d | 1667 | 6610 | 19 | 6800 | 10.9 | 41.6 |  |
|  |  |  |  | 2 d | 1075 | 6840 | 19 | 6700 | 10.5 | 40.2 |  |
| died | 236 |  |  |  |  |  |  |  |  |  |  |

YT, lunge cancer, male, 44

| IFNANK times | Days from first trial | No. of WBC(× 10⁹) treated with IFN (Lymphocytes × 10⁹) | TBVL* | Days after IFNANK | IFN-α production | 2-5AS activity (pmol/dl) | NK activity (%) | WBC (/μl) | Hb (g/dl) | Pit (× 10/μl) | Side effect** |
|---|---|---|---|---|---|---|---|---|---|---|---|
| 1st | 0 | 2.7 (1.5) | 3312 ml | 0 d | 7148 | 1650 | 52 | 5000 | 14.6 | 20.9 | ND |
|  |  |  |  | 4 hr | 10520 | 3120 | 66 |  |  |  |  |
|  |  |  |  | 1 d | 9761 |  | 57 | 5100 | 14.2 |  |  |
| 2nd | 26 | 2.4 | 2268 ml | 0 d | 5409 | 1350 | 52 | 4800 | 14.3 | 22.9 | ND |
|  |  |  |  | 1 d | 2653 | 1380 | 37 |  |  |  |  |
|  |  |  |  | 2 d | 8946 |  | 50 |  |  |  |  |
| 3rd | 699 | 3.9 (2.0) | 4503 ml | o d | 4007 | 3480 | 48 | 5700 | 14.9 | 31 | ND |
|  |  |  |  | 1 d | 2619 | 1950 | 21 | 4200 | 13.2 | 28.1 |  |
| died | 197 |  |  |  |  |  |  |  |  |  |  |

MT, Uterine cancer, female, 53

| IFNANK times | Days from first trial | No. of WBC(× 10⁹) treated with IFN (Lymphocytes × 10⁹) | TBVL* | Days after IFNANK | IFN-α production | 2-5AS activity (pmol/dl) | NK activity (%) | WBC (/μl) | Hb (g/dl) | Pit (× 10/μl) | Side effect** |
|---|---|---|---|---|---|---|---|---|---|---|---|
| 1st | 0 | 2.9 (2.2) | 3650 ml | 0 d | 1358 |  | 12 | 4200 | 12.1 | 26.7 | ND |
|  |  |  |  | 1 d | 1790 |  | 0 | 3600 | 12.5 | 27.4 |  |
|  |  |  |  | 2 d | 2425 |  | 14 | 4300 | 11.9 | 26.6 |  |
| 2nd | 210 | 3.2 (2.8) | 3593 ml | 0 d | 1389 |  | 27 | 4800 | 11.7 | 25.2 | ND |
|  |  |  |  | 2 d | 11224 |  | 12 | 4100 | 11.1 | 21 |  |
| 3rd | 230 | 3.0 (2.3) | 3335 ml | 0 d | 2689 |  | 11 | 5700 | 11.8 | 24.4 | ND |
|  |  |  |  | 1 d | 1466 |  | 8 | 4400 | 11.4 | 22.3 |  |
|  |  |  |  | 2 d | 1316 |  | 19 | 4600 | 11.6 | 23 |  |

NK, Lung cancer, male, 39

| IFNANK times | Days from first trial | No. of WBC(× 10⁹) treated with IFN (Lymphocytes × 10⁹) | TBVL* | Days after IFNANK | IFN-α production | 2-5AS activity (pmol/dl) | NK activity (%) | WBC (/μl) | Hb (g/dl) | Pit (× 10/μl) | Side effect** |
|---|---|---|---|---|---|---|---|---|---|---|---|
| 1st | 0 | 2.2 | 3934 ml | 0 d | 5145 | 3750 | 17 | 3900 | 11.5 | 22.9 | ND |
|  |  |  |  | 4 hr | 22322 | 6330 | 8 | 4900 | 10.9 | 23.2 |  |
|  |  |  |  | 1 d | 7879 | 19500 | 23 | 4200 | 12.1 | 23.5 |  |
|  |  |  |  | 4 d |  |  | 27 |  |  |  |  |
|  |  |  |  | 5 d | 9317 |  | 22 | 4300 | 11.9 | 22.3 |  |
| 2nd | 62 | 4.38 (2.3) | 4002 ml | 0 d | 10388 |  | 35 | 5000 | 11.6 | 25 | ND |
|  |  |  |  | 1 d | 14225 | 4110 | 13 | 4000 | 10.8 | 23.5 |  |
|  |  |  |  | 2 d | 9921 | 4440 | 31 | 4400 | 11.2 | 25.4 |  |
| 3rd | 92 | 3.8 (2.9) | 4001 ml | 0 d | 11485 | 2580 | 49 | 5300 | 11.7 | 20.4 | ND |
|  |  |  |  | 3 d | 7075 | 5640 | 39 | 5400 | 11.9 | 19.7 |  |
| 4th | 116 | 3.5 (3.0) | 4002 ml | 0 d | 6352 |  | 28 | 4700 | 12.7 | 18.9 | ND |
|  |  |  |  | 1 d | 9043 |  | 20 | 4800 | 11.8 | 19.2 |  |
|  |  |  |  | 4 d | 10120 |  | 22 | 5000 | 12 | 18.2 |  |
| 5th | 148 | 3.9 (2.8) | 3820 ml | 0 d | 13147 |  | 47 | 5900 | 12 | 18 | ND |
|  |  |  |  | 3 d | 10089 |  | 22 | 6400 | 11.9 | 19.1 |  |
|  |  |  |  | 6 d |  |  | 35 |  |  |  |  |
| 6th | 175 | 2.7 (1.4) | 4241 ml | 0 d | 6881 |  | 37 | 4900 | 12.7 | 16.4 | ND |
|  |  |  |  | 1 d | 9018 |  | 27 |  |  |  |  |
|  |  |  |  | 4 d | 12572 |  | 14 | 5000 | 11.9 | 14 |  |
| 7th | 195 | 2.8 (1.1) | 3943 ml | 0 d | 7493 |  | 12 | 6900 | 11.2 | 14.4 | ND |
|  |  |  |  | 1 d | 6228 |  | 25 | 6200 | 11.3 | 13.4 |  |
|  |  |  |  | 2 d | 6423 |  | 16 | 7200 | 11.5 | 12.2 |  |

TA, ATL, female, 47

| IFNANK times | Days from first trial | No. of WBC(× 10⁹) treated with IFN (Lymphocytes × 10⁹) | TBVL* | Days after IFNANK | IFN-α production | 2-5AS activity (pmol/dl) | NK activity (%) | WBC (/μl) | Hb (g/dl) | Pit (× 10/μl) | Side effect** |
|---|---|---|---|---|---|---|---|---|---|---|---|
| 1st | 0 | 3.1 | 3134 ml | 0 d | 6770 | 1950 | 8 | 5500 | 12.3 | 19 | ND |
|  |  |  |  | 1 d | 6883 | 5910 | 7 | 5300 | 13.5 | 21.4 |  |
|  |  |  |  | 4 d | 7369 | 6191 | 10 | 7500 | 13.2 | 22.5 |  |

YM, Melanona, female, 65

| IFNANK times | Days from first trial | No. of WBC(× 10⁹) treated with IFN (Lymphocytes × 10⁹) | TBVL* | Days after IFNANK | IFN-α production | 2-5AS activity (pmol/dl) | NK activity (%) | WBC (/μl) | Hb (g/dl) | Pit (× 10/μl) | Side effect** |
|---|---|---|---|---|---|---|---|---|---|---|---|
| 1st | 0 |  | — | 0 d | 4664 | 10350 | 14 | 4600 | 9.5 | 29.7 | ND |
|  |  |  |  | 1 d | 2805 | 7290 | 5 | 3300 | 10.4 | 30.9 |  |
|  |  |  |  | 2 d | 798 | 7620 | 4 | 4900 | 11.1 | 32.3 |  |
| 2nd | 12 |  |  | 0 d | 452 | 5700 | 16 | 5000 | 9.9 | 34 | ND |
|  |  |  |  | 2 d | 454 | 3690 | 19 | 3800 | 10 | 32.9 |  |
|  |  |  |  | 4 d | 704 | 8310 | 11 | 7400 | 10.5 | 26.8 |  |

YM, Lung cancer, female, 58

| IFNANK times | Days from first trial | No. of WBC(× 10⁹) treated with IFN (Lymphocytes × 10⁹) | TBVL* | Days after IFNANK | IFN-α production | 2-5AS activity (pmol/dl) | NK activity (%) | WBC (/μl) | Hb (g/dl) | Pit (× 10/μl) | Side effect** |
|---|---|---|---|---|---|---|---|---|---|---|---|
| 1st | 0 | 4.6 (2.0) | 3533 ml | 0 d | 5386 | 3210 | 37 | 4200 | 13.1 | 16.6 | ND |
|  |  |  |  | 1 d | 3124 | 7350 | 36 | 4300 | 12 | 16.8 |  |
|  |  |  |  | 4 d | 2348 | 1950 | 43 | 4900 | 13 | 18.2 |  |

TABLE 2-a-continued

Results of IFNANK therapy

| IFNANK times | Days from first trial | No. of WBC(× 10⁹) treated with IFN (Lymphocytes × 10⁹) | TBVL* | Days after IFNANK | IFN-α production | 2-5AS activity (pmol/dl) | NK activity (%) | WBC (/μl) | Hb (g/dl) | Plt (× 10/μl) | Side effect** |
|---|---|---|---|---|---|---|---|---|---|---|---|
| \multicolumn{12}{c}{HM, Ovarian cancer, female, 41} |
| 1st | 0 | 2.6 (1.8) | 2505 ml | 0 d | 1904 | | 60 | 5900 | 10.1 | 41.1 | ND |
| | | | | 1 d | 3688 | | 30 | 5800 | 9.1 | 39.6 | |
| | | | | 4 d | 7560 | | 49 | 6600 | 9.4 | 39.4 | |
| 2nd | 7 | 1.5 (1.3) | 2009 ml | 0 d | 4278 | | 15 | 6900 | 8.9 | 44.5 | ND |
| | | | | 1 d | 7344 | | 22 | 7700 | 9 | 45.5 | |
| died | 73 | | | | | | | | | | |
| \multicolumn{12}{c}{Healthy Person SH, male, 57} |
| 1st | 0 | 7.6 (5.5) | 5200 ml | 0 d | 8525 | 6150 | 53 | 6700 | 15.4 | | ND |
| | | | | 2 h | 14097 | 6180 | 50 | 5200 | 12.6 | | |
| | | | | 17 h | 1864 | 6930 | 57 | | | | |
| | | | | 1 d | 9770 | 7500 | 61 | | | | |
| | | | | 2 d | 3736 | 7110 | 65 | | | | |
| | | | | 4 d | 15809 | 5520 | 72 | | | | |
| \multicolumn{12}{c}{YR, male, 43} |
| 1st | 0 | 6.0 (4.0) | 4750 ml | 0 d | 8757 | 1110 | 32 | 6000 | 15.2 | | ND |
| | | | | 1 d | 13748 | 4620 | 39 | | | | |
| | | | | 2 d | 9014 | 4080 | 47 | | | | |
| \multicolumn{12}{c}{YS, male, 59} |
| 1st | 0 | 6 | 4600 ml | 0 d | 13452 | 2190 | 50 | | | | ND |
| | | | | 1 d | 9948 | 4050 | 45 | | | | |
| | | | | 2 d | 8561 | 5280 | 40 | | | | |
| \multicolumn{12}{c}{YH, female, 32} |
| 1st | 0 | 2.9 | 3000 ml | 0 d | 6872 | 1710 | 14 | | | | |
| | | | | 1 d | 7444 | 3900 | 10 | | | | |
| | | | | 2 d | 12914 | 5010 | 34 | | | | |
| | | | | 3 d | 6561 | 3600 | 8 | | | | |
| | | | | 4 d | 4890 | 3180 | 12 | | | | |

[*Total blood volume circulated through leukopheretic apparatus.
**Fever(>37° C.), Malaise, Leukopenia(>3000/μl), Thrombocytopenia(<10⁴/μl)]

I claim:

1. A method for treating a patient with cancer, which comprises collecting lymphocytes from the patient by leukopheresis, contacting the lymphocytes with interferon-α in vitro for a term effective to potentiate the immunological activity of the lymphocytes, and then returning the lymphocytes to the patient intravenously.

2. A method according to claim 1, wherein the interferon-α is in a concentration of 10 to 1000 IU/ml.

3. A method according to claim 1, wherein the immunological activity is the activity of natural killer cells or (2'-5')-oligoadenylate, or the ability of producing interferon-α.

4. A method according to claim 1, wherein the term for contacting lymphocytes with interferon-α is 1 to 2 hours.

5. A method according to claim 2 wherein the interferon-α is in a concentration of 300 to 500 IU/ml.

6. A method according to claim 4 wherein the term is about 1.5 hours.

7. A method for treating a patient with cancer, which comprises collecting lymphocytes from the patient by leukopheresis, contacting in vitro, the lymphocytes with interferon-alpha in an amount which is effective to potentiate the immunological activity of the lymphocytes when administered to the patient for a short term, and then returning, intravenously, the lymphocytes together with the interferon-alpha to the patient.

8. A method according to claim 7, wherein the lymphocytes are contacted with interferon-alpha in a concentration of 100 to 500 IU/ml.

9. A method according to claim 7, wherein the lymphocytes are contacted with interferon-alpha in a concentration of 300 to 500 IU/ml.

10. A method according to claim 7, wherein about 200–300 ml. of the lymphocyte-rich fraction is collected by leukopheresis.

11. A method according to claim 7, wherein about 100,000 IU of interferon-alpha is contacted with the collected lymphocytes.

12. A method according to claim 7, wherein the term for contacting lymphocytes with interferon-alpha is 1 to 2 hours.

13. A method according to claim 12 wherein the term is about 1.5 hours.

14. A method for potentiating lymphocytes which comprises collecting lymphocytes from a patient by leukopheresis, contacting the collected lymphocytes with interferon-alpha in an amount which is effective to potentiate the immunological activity of the lymphocytes when administered to the patient in vitro for a short term effective to potentiate the immunological activity of the lymphocytes, and returning the treated lymphocytes to the patient.

15. A method according to claim 14 wherein the immunological activity is the activity of natural killer cells or (2'–5')-oligoadenylase, or the ability of producing interferon-α.

16. A method according to claim 14 wherein the term for contacting lymphocytes with interferon-α is 1 to 2 hours.

17. A method according to claim 16 wherein the term is about 1.5 hours.

18. A method according to claim 14 wherein the interferon-alpha is in a concentration of 100 to 500 IU/ml.

19. A method according to claim 18 wherein the interferon-α is in aconcentration of 300 to 500 IU/ml.

20. A method according claim 14 wherein about 200–300 ml of the lymphocyte-rich fraction is collected by leukopheresis.

21. A method according to claim 14, wherein about 100,000 IU of interferon-alpha is contacted with the collected lymphocytes.

* * * * *

UNITED STATES PATENT AND TRADEMARK OFFICE
CERTIFICATE OF CORRECTION

PATENT NO. : 5,846,928
DATED : December 8, 1998
INVENTOR(S) : Tsunataro Kishida

It is certified that error appears in the above-indentified patent and that said Letters Patent is hereby corrected as shown below:

Column 1, line 43 and Column 2, line 32: "HK" should read --NK--.

Column 2, lines 40-41 should read on the same line: --M. et. al.; Hepatology 8, 366-370, 1988).--

Column 4, line 7: "a anti-" should read --an anti- --

Column 5, Table 2-a, the second patient "YT, lunge, male, 44" should read --YT Lung cancer, male, 44-- and in the same Table, line 11 from the bottom "YM, Melanona, female, 65" should read --YM, Melanoma, female, 65--

Signed and Sealed this

Twenty-fifth Day of May, 1999

Attest:

Attesting Officer

Q. TODD DICKINSON

Acting Commissioner of Patents and Trademarks